| United States Patent [19] | [11] Patent Number: 4,772,460 |
| Malook et al. | [45] Date of Patent: Sep. 20, 1988 |

[54] METHOD OF REDUCING THE SWELLING OR PAIN ASSOCIATED WITH ANTIBIOTICS COMPOSITIONS

[75] Inventors: Saif U. Malook, Newry, Northern Ireland; Peter F. G. Boon, Horsham, England; James P. Morgan, Navan, Ireland

[73] Assignee: Bimeda Research and Development, Ltd., Dublin, Ireland

[21] Appl. No.: 914,731

[22] Filed: Oct. 1, 1986

[30] Foreign Application Priority Data

Oct. 1, 1985 [IE] Ireland ................................. 2408/85

[51] Int. Cl.⁴ ...................... A61K 31/79; A61K 31/65
[52] U.S. Cl. ........................................ 424/10; 424/80; 514/152; 514/153

[58] Field of Search .................... 424/80, 10; 514/152, 514/153

[56] References Cited

U.S. PATENT DOCUMENTS

| 3,557,280 | 1/1971 | Weber et al. | 424/80 |
| 3,674,859 | 7/1972 | Beutel et al. | 424/80 |
| 3,957,972 | 5/1976 | Weber et al. | 424/80 |
| 4,018,889 | 4/1977 | Armstrong | 424/80 |
| 4,081,528 | 3/1978 | Armstrong | 424/80 |
| 4,259,331 | 3/1981 | Armstrong | 424/80 |

*Primary Examiner*—Jerome D. Goldberg
*Attorney, Agent, or Firm*—Iver P. Cooper

[57] ABSTRACT

Oxytetracycline aqueous solutions, particularly for parenteral administration containing N-Methylpyrollidone as a solvent are disclosed.

18 Claims, No Drawings

METHOD OF REDUCING THE SWELLING OR PAIN ASSOCIATED WITH ANTIBIOTICS COMPOSITIONS

BACKGROUND TO THE INVENTION

The invention relates to antibiotic compositions including a tetracycline-type compound. The term "tetracycline-type" compound refers to tetracycline, chlortetracycline, doxycycline and particularly oxytetracycline or their pharmacologically acceptable salts, especially the dihydrate salt of oxytetracycline.

It is known in the art to use 2 pyrollidone as a co-solvent in the preparation of an aqueous solution containing more than 20% by weight of oxytetracycline. The intramuscular injection of such solutions however is relatively painful and may be accompanied by a necrotic reaction at the site of injection.

OBJECTS OF THE INVENTION

One object of the invention is to provide a stable solution of a tetracycline-type compound, particularly oxytetracycline, which is particularly suitable for parenteral administration with minimum pain, irritancy and necrotic reaction at the injection site.

A further object of the invention is to provide a stable clear solution of a chelated tetracycline, particularly oxytetracycline, which has a long shelf life, particularly when presented in a multi-dose container.

Another object of the invention is to provide a process for the preparation of such a composition.

These and other objects of the invention will be apparent from the following no-limiting description thereof.

SUMMARY OF THE INVENTION

According to the invention there is provided a tetracycline-type composition in the form of an aqueous solution comprising:

from 10 to 45% by weight of a tetracycline-type compound;

a magnesium compound soluble in the solution, said compound being provided in an amount which is from 5% to 15% by weight of the amount of tetracycline-type compound provided and;

from 25 to 50% by weight of N-methylpyrrollidone, the composition having a pH of from 7.5 to 9.5.

In a particularly preferred embodiment of the invention the composition includes polyvinylpyrrolidone having an average molecular weight of between 1,000 and 30,000 in a concentration of from 1 to 10% by weight. Preferably the average molecular weight of the polyvinylpyrrolidone is between 2,000 and 20,000. Especially preferred is polyvinylpyrrollidone having an average molecular weight of between 9,000 and 11,000.

In a preferred embodiment of the invention the composition includes an anti-oxidant in a concentration of between 0.1% and 2% by weight. Preferably the antioxidant is sodium formaldehyde sulphoxylate whch is present in a concentrate of between 0.4% to 0.6% by weight.

In one embodiment of the invention the tetracycline-type compound is oxytetracycline or a pharmacologically acceptable salt thereof. For compositions of between 20 and 45% preferably the tetracycline-type compound is oxytetracycline dihydrate salt and the magnesium compound is magnesium oxide. For compositions of between 10 and 20% preferably the tetracycline-type compound is oxytetracycline hydrochloride salt and the magnesium compound is magnesium chloride.

In a preferred embodiment of the invention the N-methylpyrrolidone is present in an amount of 35% to 45% by weight.

The invention particularly provides an oxytetracycline composition in the form of an aqueous solution comprising:

from 10 to 40% by weight of oxytetracycline or a pharmacologically acceptable salt thereof;

a magnesium compound soluble in the solution, said compound being provided in an amount which is from 5% to 15% by weight of the amount of oxytetracycline provided and;

from 25 to 50% by weight of N-methylpyrrolidone; and from 1 to 10% by weight of polyvinylpyrrolidone having an average molecular weight of between 2,000 and 20,000;

the composition having a pH of from 7.5 to 9.5.

More particularly the invention provides an oxytetracycline composition in the form of an aqueous solution comprising:

from 10 to 40% by weight of oxytetracycline or a pharmacologically acceptable salt thereof;

a mangesium compound soluble in the solution, said compound being provided in an amount which is from 5% to 15% by weight of the amount of oxytetracycline provided;

from 25 to 50% by weight of N-methylpyrollidone;

from 1 to 10% by weight of polyvinylpyrollidone having an average molecular weight of between 2,000 and 20,000; and from 0.1% to 2% by weight of an anti-oxidant, the composition having a pH of from 7.5 to 9.5.

More especially the invention provides an oxytetracycline composition in the form of an aqueous solution comprising;

from 20 to 40% by weight of oxytetracycline dihydrate salt;

a magnesium compound soluble in the solution, said compound being provided in an amount which is from 5% to 15% by weight of the amount of oxytetracycline provided;

from 35% to 40% by weight of N-methylpyrrolidone; and from 0.1% to 2% by weight of an anti-oxidant; the composition having a pH of from 7.5 to 9.5

A particularly preferred oxytetracycline composition comprises from 20 to 25% by weight of oxytetracycline dihydrate salt;

a magnesium compound soluble in the solution, said compound being provided in an amount which is from 7% to 10% by weight of the amount of oxytetracycline provided;

from 35% to 40% by weight of N-methylpyrollidone;

from 1 to 10% by weight of polyvinylpyrrolidone having an average molecular weight of between 9,000 and 11,000; and from 0.4 to 0.6% by weight of an anti-oxidant;

the composition having a pH of from 7.5 to 9.5.

The invention also provides a process for preparing the tetracycline-type composition comprising the steps of:

adding N-methylpyrrolidone to water, adding the magnesium compound and suspending it in the solvent, adding a portion of the anti-oxidant to the mixture, adding the tetracycline-type compound while stirring without aeration, mixing the solution, adding the balance of the anti-oxidant to the solution, filtering the solution, and, if necessary adjusting the pH to the desired range.

The preferred process for preparing the most preferred oxytetracycline composition comprises the steps of:

adding N-methylpyrollidone to water heated to between 75° and 85° C., adding polyvinylpyrollidone to the mixture, heating the mixture to approximately 75° C., adding magnesium oxide and suspending it in the solvent, adding a portion of the anti-oxidant to the mixture, adding oxytetracycline dihydrate in small portions while stirring without aeration, mixing the solution for between 5 and 10 minutes, adding the balance of the anti-oxidant to the solution, filtering the solution, and, if necessary adjusting the pH to the desired range.

DETAILED DESCRIPTION OF THE INVENTION

Example 1

An injectable solution having the following formulation was prepared.

|  | gm/1000 ml |
| --- | --- |
| Oxytetracycline Dihydrate | 231.0 |
| Magnesium Oxide | 19.04 |
| N—Methylpyrollidone | 440.58 |
| Polyvinylpyrrolidone K-17 Pf | 25.0 |
| Sodium formaldehyde sulfoxylate | 5.0 |
| Monoethanolomine | q.s. to pH 8.8 to 9.2 |
| Water for Injection | 527.0 |
|  | (q.s. to 1000 ml) |

The solution is prepared while maintaining a stream of nitrogen to exclude oxygen. The solvent was prepared by first placing water for injection and N-methylpyrrolidone in a batch vessel and then adding to the polyvinylpyrrolidone with gentle stirring. Using direct heat and solvent is then heated to approximately 75° C. The magnesium oxide is then added and suspended in the solvent after which one third of the antioxidant, sodium formaldehyde sulfoxylate is added to improve the colour of the mixture. Oxytetracycline didhydrate is then added in small portions with continued stirring but without aeration. When all the oxytetracycline has been added the solution is mixed well without aeration, for between 5 and 10 minutes to ensure complete dissolution.

The remaining antioxidant is then added to the solution to provide an excess which is used to maintain the clear colour of the solution and prevents darkening on storage.

The solution is then filtered through a prefilter and the pH is adjusted to 8.8 to 9.2 at 20° C. if necessary, using ethanolomine and after cooling the solution is sterilised by filtering it through a 0.2μ filter before being filled into containers. Nitrogen cover is maintained during the process.

The solution prepared had a specific gravity of approximately 1.2 at 20° C.

Example 2

Following the method of Example 1 an injectable solution having the following formulation was prepared

|  | gm/1000 ml |
| --- | --- |
| Oxytetracycline Dihydrate | 226.5 |
| Magnesium Oxide | 19.2 |
| N—Methylpyrollidone | 420.0 |
| Polyvinylpyrollidone K-17 Pf | 50.0 |
| Sodium Formaldehyde Sulfoxylate | 10.0 |
| Monoethanolamine | ·5.75 |
| Water for Injection | q.s. to 1000 ml. |

The pH of the solution at 20° C. was 8.5 to 9.5. The specific gravity (g/ml) was 1.13 to 1.15 at 20° C.

We have also prepared an injectable solution having 20% oxytetracycline using N-methylpyrollidone alone as a solvent. The formulation for this solution is given in Example 3.

Example 3

|  | gm/1000 ml |
| --- | --- |
| Oxytetracycline Dihydrate | 226.5 |
| Magnesium Oxide | 19.2 |
| N—Methylpyrollidone | 480.0 |
| Sodium Formaldehyde Sulfoxylate | 10.0 |
| Monoethanolomine | 5.75 |
| Water for injection | q.s. to 1000 ml. |

We have also prepared injectable solutions having 10%, 30% and 40% oxytetracycline using N-methylpyrollidone as a solvent. The formulations and method of preparing these solutions are given in Examples 4 to 6 below.

Example 4

Following the procedure of Example 4 an injectable solution having the following formulation was prepared:

|  | gm/1000 ml |
| --- | --- |
| Oxytetracycline Dihydrate | 350 |
| Magnesium Oxide | 28.5 |
| N—Methylpyrollidone | 400.0 |
| Sodium formaldehyde sulfoxylate | 5.0 |
| Monoethanolomine | q.s. to pH 8.8 to 9.2 |
| Water for Injection | q.s. to 1000 ml. |

The solution prepared has an S.G. of approximately 1.16 at 20° C.

This formulation was prepared following the procedure of Example 1 with the exception that polyvinylpyrollidone is ommitted.

The solution prepared had an S.G. of approximately 1.1 at 20° C.

Example 5

An injectable solution having the following formulation was prepared:

|  | gm/1000 ml |
| --- | --- |
| Oxytetracycline Dihydrate | 400 |

-continued

|  | gm/1000 ml |
|---|---|
| Magnesium Oxide | 32.6 |
| N—methylpyrollidone | 380 |
| Sodium formaldehyde sulfoxylate | 5.0 |
| Water | q.s. to 1000 ml |
| Monoethanolomine | q.s. to pH 8.8 to 9.2 |

The procedure is the same as that of Example 2 with the exception that the monoethanolomine is added before the magnesium oxide and oxytetracycline.

The solution had an S.G. of approximately 1.19.

Example 6

An injectable solution having the following formulation was prepared:

|  | gm/1000ml |
|---|---|
| Oxytetracycline hydrochloride | 103.0 |
| Magnesium Chloride.6(H$_2$O) | 51.5 |
| N—methylpyrollidone | 450.0 |
| Sodium formaldehyde sulfoxylate | 5.0 |
| Monethanolomine | q.s. to pH 8 8 to 9.2 |
| Water for injection | q.s. to 1,000 ml. |

The solution is prepared while maintaining a stream of nitrogen to exclude oxygen.

Water is placed in a batch vessel and the magnesium chloride and portion of the antioxidant are added and dissolved with gentle stirring. The N-methylpyrrolidone is added and a homogeneous solution is obtained with gentle stirring. The oxytetracycline hydrochloride is then added and dissolved again with gentle stirring. The remaining antioxidant is then added to the solution to provide an excess which maintains a clear colour of the solution and prevents darkening on storage.

The solution is filtered through a prefilter and the pH is adjusted to 8.8 to 9.2 at 20° C. using monoethanolomine.

The solution prepared had an S.G. of approximately 1.1 at 20° C.

We have found that the water to N-methylpyrrolidone ratio is important in ensuring that no precipitation occurs during the course of the preparation process or in storage.

We have also found that the addition of the antioxidant, in this case sodium formaldehyde sulfoxylate, in two stages ensures that a clear solution is obtained, and because of the excess anti-oxidant used, maintained over a long life in storage. This is particularly important as the solution is usually provided in multi-dose containers and the excess anti-oxidant used prevents darkening of the solution between uses.

We have found that the oxytetracycline composition of Example 2 has maintained colour with no sedimentation or precipitation or appreciable change in pH or oxytetracycline composition over long periods.

Uses

Intramuscular injection of the solutions results in sustained therapeutic blood levels of Oyxtetracycline. The solutions are indicated in the treatment and control of diseases caused by or associated with organisms sensitive to Oxytetracycline, which includes many gram-positive and gram-negative bacteria, some protozoa, rickettsiae, mycoplasmas and chlamydiae.

INDICATIONS

Cattle:
For the treatment of Pneumonia, Pasteurellosis, Foul-In-The-Foot, Actinobacillosis, Joint Ill and supportive therapy in mastitis. For the treatment of Anaplasmosis, Streptrothricosos, and Heartwater where these conditions are known to occur. For the treatment and control of post-parturient and post-operative infections.

Sheep:
For the treatment of Pneumonia, Metritis, Foot-Rot, Joint Ill. For the treatment and control of post-parturient and post-operative infections.

Pigs:
For the treatment of Pneumonia, Mastitis, Erysipelas, Joint Ill. For the treatment and control of the Mastitis-Metritis-Agalactia syndrome, post-operative infections and Pasteurellosis.

DOSAGE & ADMINISTRATION

The solutions are administered by deep intramuscular injection at the rate of approximately 1 ml. per 10 kg. which is equivalent to 20 mg. per kg.

Milk residue studies conducted on lactating cows in accordance with standard test methods showed that at 120 hours post administration the milk was free from antibiotic residues and remained free through 168 hours.

Test trials on the efficacy of the composition were conducted on several cows including animals suffering from mastitis, pyrexia, pneumonia, foul foot, actenabacillus and other complaints. All responded very satisfactorily to deep intra-muscular injection at a rate of 1 ml per 10 kg body weight.

N-methylpyrrolidone which is also referred to as 1-methyl-2-pyrrolidone and has the chemical formula

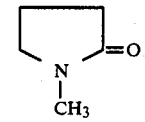

is a colourless mobile liquid with a faint amine odour. Its boiling point range is 202.5° to 205° C., making it a very stable solvent.

We have surprisingly found that the use of this solvent instead of 2-pyrollidone gives an injectable solution which causes less irritation at the injection site than a corresponding solution with 2-pyrollidone.

Example 7

A double blind trial was done to compare the irritancy of the formulation of Example 2 with a formulation using 2-pyrollidone as a solvent.

14 cattle weighing on average 650 kgs. were injected into the neck muscle at 3 sites with 20 ml. at each site.

Product A, the identity of which was unknown to the veterinary surgeon administering it, was injected into the right side of the neck on day 1. The behaviour of the animals at the time of injection and for up to 30 minutes later, was observed and recorded by the vet. Some two hours later the injection site was again examined for signs of swelling, heat and pain, and the findings were recorded. At 24 hours post-injection the injection sites were again inspected and the results were recorded.

On days 3 and 4 the same procedure was followed using Product B, the identity of which was again unknown to the vet administering the injection. An evaluation of comparative irritancy was then made of the formulations.

The results are summarised in the following Table.

| PRODUCT | NUMBER OF ANIMALS (1) SHOWING IMMEDIATE POST-INJECTION PAIN | SWELLING AT INJECTION SITE | |
|---|---|---|---|
| | | 2 hours | 24 hours |
| based on 2-pyrollidone | 10 | 2 | 3 |
| Formulation of Example 2 | 2 | 2 | 2 |

(1) The discomfort noted in the immediate post injection period consisted of:
Head shaking,
Neck twisting,
Rapid extensions of the neck.
Less easily interpretable featuures were:
Yawning,
Drooling of saliva.

While the invention has been described with reference to oxytetracycline compositions it is envisaged that it may also be applied to other tetracycline-type compounds including doxycycline, tetracycline and chlortetracycline and pharmacologically acceptable salts thereof.

We claim:

1. A method of reducing the swelling or pain associated with the administration of a tetracycline-type compound, which comprises administering by injection to an animal in need thereof a tetracycline-type composition comprising an aqueous solution of:
   from 10 to 45% by weight of a tetracycline-type compound;
   a magnesium compound soluble in the solution, said compound being provided in an amount which is from 5% to 15% by weight of the amount of tetracycline-type compound provided and;
   from 25 to 50% by weight of N-methylpyrollidone, the composition having a pH of from 7.5 to 9.5, said N-methyl pyrollidone being administered in an amount effective to reduce pain or swelling attributable to the tetracycline-type compound.

2. The method as claimed in claim 1 wherein the composition includes polyvinylpyrollidone having an average molecular weight of between 1,000 and 30,000 in a concentration of from 1 to 10% by weight.

3. The method as claimed in claim 2 wherein the average molecular weight of the polyvinylpyrollidone is between 2,000 and 20,000.

4. The method as claimed in claim 3 wherein the average molecular weight of the polyvinylpyrollidone is between 9,000 and 11,000.

5. The method as claimed in claim 1 including an anti-oxidant in a concentration of betweenn 0.1% and 2% by weight.

6. The method as claimed in claim 5 wherein the anti-oxidant is sodium formaldehyde sulphoxylate which is present in a concentration of between 0.4% to 0.6 % by weight.

7. The method as claimed in claim 1 wherein the tetracycline-type compound is oxytetracycline or a pharmacologically acceptable salt thereof.

8. The method as claimed in claim 7 wherein the tetracycline-type compound is oxytetracycline dihydrate salt.

9. The method as claimed in claim 8 wherein the magnesium compound is magnesium oxide.

10. The method as claimed in claim 8 wherein the oxytetracycline dihydrate is present in an amount of between 20 and 46% by weight.

11. The method as claimed in claim 7 wherein the tetracycline-type compound is oxytetracycline hydrochloride.

12. The method as claimed in claim 11 wherein the magnesium compound is magnesium chloride.

13. The method as claimed in claim 11 wherein the oxytetracycline hydrochloride is present in an amount of between 10 and 20% by weight.

14. The method as claimed in claim 1 wherein the N-methylpyrollidone is present in an amount of between 35% to 45% by weight.

15. A method of reducing the swelling or pain associated with the administration of an oxytetracycline which comprises administering by injection to an animal in need thereof an oxytetracycline composition comprising an aqueous solution of:
   from 10 to 40% by weight of oxytetracycline or a pharmacologically acceptable salt thereof;
   a magnesium compound soluble in the solution, said compound being provided in an amount which is from 5% to 15% by weight of the amount of oxytetracycline provided and;
   from 25 to 50% by weight of N-methylpyrollidone; and
   from 1 to 10% by weight of polyvinylpyrrolidone having an average molecular weight of between 2,000 and 20,000;
   the composition having a pH of from 7.5 to 9.5, said N-methyl pyrollidone being administered in an amount effective to reduce pain or swelling attributable to the oxytetracycline.

16. A method of reducing the swelling or pain associated with the administration of an oxytetracycline which comprises administering by injection to an animal in need thereof an oxytetracycline composition comprising an aqueous solution of:
   from 10 to 40% by weight of oxytetracycline or a pharmacologically acceptable salt thereof;
   a magnesium compound soluble in the solution, said compound being provided in an amount which is from 5% to 15% by weight of the amount of oxytetracycline provided;
   from 25 to 50% by weight of N-methylpyrollidone;
   from 1 to 10% by weight of polyvinylpyrrolidone having an average molecular weight of between 2,000 and 20,000; and
   from 0.1% to 2% by weight of an anti-oxidant, the composition having a pH of from 7.5 to 9.5, said N-methyl pyrrolidone being administered in an amount effective to reduce pain or swelling attributable to the oxytetracycline.

17. A method of reducing the swelling or pain associated with the administration of an oxytetracycline which comprises administering by injection to an animal in need thereof an oxytetracycline composition comprising an aqueous solution of:
   from 20 to 40% by weight of oxytetracycline dihydrate salt;
   a magnesium compound soluble in the solution, said compound being provided in an amount which is from 5% to 15% by weight of the amount of oxytetracycline provided;
from 35% to 40% by weight of N-methylpyrrolidone; and
from 0.1% to 2% by weight of an anti-oxdant; the composition having a pH of from 7.5 to 9.5, said N-methyl pyrollidone being administered in an amount effective to reduce pain or swelling attributable to the oxytetracycline.

18. A method of reducing the swelling or pain associated with the administration of an oxytetracycline which comprises administering by injection to an animal in need thereof an oxytetracycline composition comprising an aqueous solution of:
from 20 to 25% by weight of oxytetracycline dihydrate salt;
a magnesium compound soluble in the solution, said compound being provided in an amount which is from 7% to 10% by weight of the amount of oxytetracycline provided;
from 35% to 40% by weight of N-methylpyrollidone;
from 1 to 10% by weight of polyvinylpyrrolidone having an average molecular weight of between 9,000 to 11,000; and
from 0.4 to 0.6% by weight of an anti-oxidant; the composition having a pH of from 7.5 to 9.5, said N-methyl pyrollidone being administered in an amount effective to reduce pain or swelling attributable to the oxytetracycline.

* * * * *